(12) United States Patent
Saigusa et al.

(10) Patent No.: US 11,800,219 B2
(45) Date of Patent: Oct. 24, 2023

(54) RADIATION IMAGING SYSTEM, CONTROL METHOD THEREOF, SYSTEM AND CONTROL METHOD THEREOF

(71) Applicant: CANON KABUSHIKI KAISHA, Tokyo (JP)

(72) Inventors: Akio Saigusa, Tama (JP); Akiya Nakayama, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/804,435

(22) Filed: May 27, 2022

(65) Prior Publication Data

US 2022/0294973 A1 Sep. 15, 2022

Related U.S. Application Data

(63) Continuation of application No. 16/720,833, filed on Dec. 19, 2019, now Pat. No. 11,375,098.

(30) Foreign Application Priority Data

Dec. 27, 2018 (JP) ................................. 2018-245377

(51) Int. Cl.
*H04N 23/66* (2023.01)
*G01N 23/04* (2018.01)
(Continued)

(52) U.S. Cl.
CPC ............. *H04N 23/66* (2023.01); *G01N 23/04* (2013.01); *G06F 3/14* (2013.01); *H04N 23/667* (2023.01); *G01N 2223/408* (2013.01)

(58) Field of Classification Search
CPC ...... H04N 5/23203; H04N 5/32; H04N 5/232; H04N 5/23245; H04N 5/374; H04N 23/66;
(Continued)

(56) References Cited

U.S. PATENT DOCUMENTS 7,196,725 B1 3/2007 Saigusa
8,969,820 B2 3/2015 Suwa
(Continued)

FOREIGN PATENT DOCUMENTS

JP 2007-312365 A 11/2007
JP 2011-110103 A 6/2011
(Continued)

*Primary Examiner* — Marly S Camargo
(74) *Attorney, Agent, or Firm* — VENABLE LLP

(57) ABSTRACT

A radiation imaging system comprises a radiation imaging apparatus having a plurality of imaging modes, and a control apparatus configured to control imaging of a radiation image with respect to the radiation imaging apparatus. The radiation imaging system comprises: an obtaining unit configured to obtain information with respect to a communication state between the radiation imaging apparatus and the control apparatus; and a display control unit configured to cause a display unit of at least one of the radiation imaging apparatus and the control apparatus to display information indicating a margin in the communication state based on an imaging mode of the radiation imaging apparatus and the information with respect to the communication state.

20 Claims, 9 Drawing Sheets

(51) Int. Cl.
*G06F 3/14* (2006.01)
*H04N 23/667* (2023.01)
*H04N 23/30* (2023.01)
*H04N 25/30* (2023.01)

(58) Field of Classification Search
CPC ...... H04N 23/667; H04N 23/68; H04N 23/60; H04N 25/75; H04N 23/30; H04N 25/30; G01N 23/04; G01N 2223/408; G01N 2223/306; G01N 3/04; G06F 3/14; A61B 6/4233; A61B 6/4283; A61B 6/4405; A61B 6/486; A61B 6/487; A61B 6/54; A61B 6/542; A61B 6/545; A61B 6/548; A61B 6/56; A61B 6/563; A61B 6/566; A61B 6/585; A61B 6/586; G09G 2370/16
See application file for complete search history.

(56) References Cited

U.S. PATENT DOCUMENTS

| | | | |
|---|---|---|---|
| 9,052,400 B2 | 6/2015 | Saruta | |
| 9,492,137 B2 * | 11/2016 | Iwamoto | A61B 6/563 |
| 9,788,809 B2 * | 10/2017 | Hiroike | A61B 6/00 |
| 10,610,189 B2 * | 4/2020 | Takeshima | |
| 10,708,497 B2 * | 7/2020 | Ohguri | G05B 15/02 |
| 11,166,693 B2 | 11/2021 | Saigusa | |
| 11,375,098 B2 * | 6/2022 | Saigusa | A61B 6/586 |
| 2007/0237402 A1 | 10/2007 | Dekel | |
| 2011/0222657 A1 | 9/2011 | Kobayashi | |
| 2013/0153775 A1 | 6/2013 | Nomura | |
| 2014/0079186 A1 * | 3/2014 | Kobayashi | A61B 6/4405 378/91 |
| 2014/0091225 A1 | 4/2014 | Sasaki | |
| 2014/0151769 A1 | 6/2014 | Wayama | |
| 2014/0275954 A1 | 9/2014 | Ohta | |
| 2016/0174927 A1 * | 6/2016 | Ohguri | A61B 6/563 348/77 |
| 2018/0353150 A1 * | 12/2018 | Takeshima | A61B 6/56 |
| 2019/0139666 A1 | 5/2019 | Sasaki | |
| 2019/0261931 A1 * | 8/2019 | Ross | A61B 6/547 |

FOREIGN PATENT DOCUMENTS

| | | | | |
|---|---|---|---|---|
| JP | 2015-126985 A | | 7/2015 | |
| JP | 2016-112322 A | | 6/2016 | |
| JP | 2017-94007 A | | 6/2017 | |
| JP | 2017094010 A | * | 6/2017 | ......... A61B 6/4283 |
| JP | 2018-7851 A | | 1/2018 | |

* cited by examiner

FIG. 5

| IMAGING MODE | IMAGE SIZE | BINNING | FRAME RATE | REQUIRED COMMUNICATION RATE |
|---|---|---|---|---|
| IMAGING MODE 1 | 1250x1250 | 2x2 | 10fps | 250Mbps |
| IMAGING MODE 2 | 1000x1000 | 1x1 | 5fps | 80Mbps |
| ... | ... | ... | ... | ... |
| STILL IMAGE | 2500x2500 | 1x1 | SINGLE IMAGING | 20Mbps |
| STILL IMAGE AEC | 2500x2500 | 1x1 | SINGLE IMAGING | 250Mbps |

FIG. 6

| COMMUNI-CATION STATE LEVEL | ANTENNA DISPLAY | STANDARD (IMAGING MODE UNSELECTED) | MOVING IMAGE MODE 1 | MOVING IMAGE MODE 2 | STILL IMAGE | STILL IMAGE AEC |
|---|---|---|---|---|---|---|
| 0 | NONE | DISCONNECT | DISCONNECT | DISCONNECT | DISCONNECT | DISCONNECT |
| 1 | ▫ | LOWER THAN 75Mbps | LOWER THAN 83Mbps | LOWER THAN 40Mbps | LOWER THAN 10Mbps | LOWER THAN 83Mbps |
| 2 | ▫▫ | 75 ~ LOWER THAN 150Mbps | 83 ~ 166Mbps | 40 ~ 60Mbps | 10 ~ 15Mbps | 83 ~ 166Mbps |
| 3 | ▫▫▫ | 150 ~ LOWER THAN 225Mbps | 166 ~ 250Mbps | 60 ~ 80Mbps | 15 ~ 20Mbps | 166 ~ 250Mbps |
| 4 | ▫▫▫▫ | 225 ~ 300Mbps | 250 ~ 333Mbps | 80 ~ 160Mbps | 20 ~ 50Mbps | 250 ~ 333Mbps |
| 5 | ▫▫▫▫▫ | EQUAL TO OR HIGHER THAN 300Mbps | EQUAL TO OR HIGHER THAN 333Mbps | EQUAL TO OR HIGHER THAN 160Mbps | EQUAL TO OR HIGHER THAN 50Mbps | EQUAL TO OR HIGHER THAN 333Mbps |

MARGIN: LOW ←——→ MARGIN: HIGH

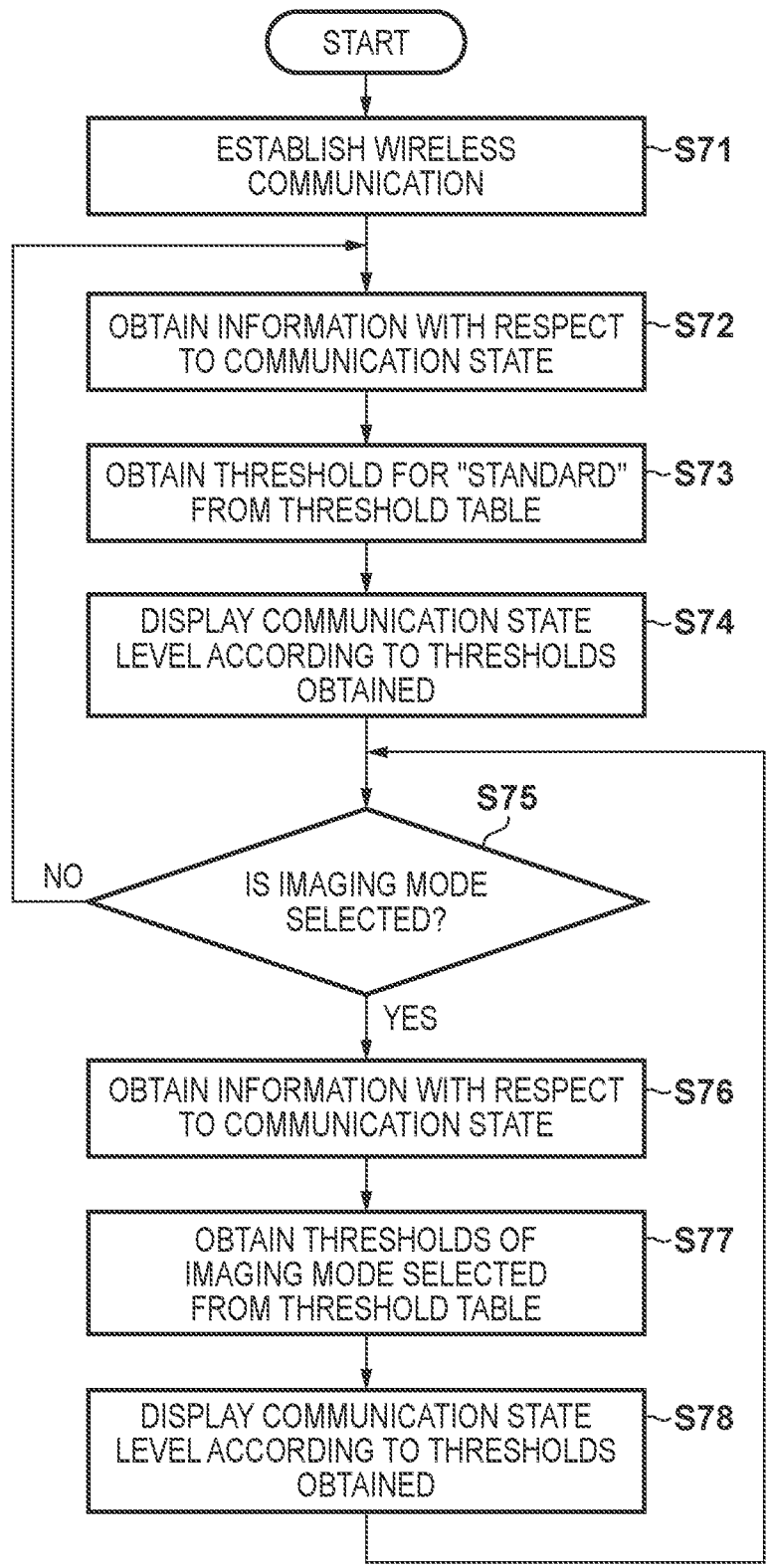

FIG. 8

| COMMUNI-CATION STATE LEVEL | ANTENNA DISPLAY COLOR | MOVING IMAGE MODE 1 | MOVING IMAGE MODE 2 | STILL IMAGE | STILL IMAGE AEC |
|---|---|---|---|---|---|
| 0 | BLACK | DISCONNECT | DISCONNECT | DISCONNECT | DISCONNECT |
| 1 | RED | LOWER THAN 83Mbps | LOWER THAN 40Mbps | LOWER THAN 10Mbps | LOWER THAN 83Mbps |
| 2 | ORANGE | 83 ~ 166Mbps | 40 ~ 60Mbps | 10 ~ 15Mbps | 83 ~ 166Mbps |
| 3 | YELLOW | 166 ~ 250Mbps | 60 ~ 80Mbps | 15 ~ 20Mbps | 166 ~ 250Mbps |
| 4 | YELLOWISH GREEN | 250 ~ 333Mbps | 80 ~ 160Mbps | 20 ~ 50Mbps | 250 ~ 333Mbps |
| 5 | GREEN | EQUAL TO OR HIGHER THAN 333Mbps | EQUAL TO OR HIGHER THAN 160Mbps | EQUAL TO OR HIGHER THAN 50Mbps | EQUAL TO OR HIGHER THAN 333Mbps |

MARGIN: LOW ←——————→ MARGIN: HIGH

RADIATION IMAGING SYSTEM, CONTROL METHOD THEREOF, SYSTEM AND CONTROL METHOD THEREOF

BACKGROUND OF THE INVENTION

Field of the Invention

The present invention relates to a radiation imaging system, a control method thereof, a system and a control method thereof.

Description of the Related Art

In recent years, in a radiation imaging system widely used in the industrial field, medical field, and the like, a portable radiation imaging apparatus capable of imaging in a plurality of imaging modes, such as still image capturing and moving image capturing, suitable for purposes has been studied. A portable radiation imaging apparatus often communicates with a control apparatus using wireless communication to improve portability.

Japanese Patent Laid-Open No. 2018-7851 discloses an example of the radiation imaging system that performs still image capturing and moving image capturing using wireless communication between a radiation imaging apparatus and a control apparatus.

A wireless communication environment changes from time to time due to the distance between apparatuses that communicate with each other, obstacles therebetween, radio wave interference from another wireless communication apparatus, or the like. As the wireless communication environment changes, the stability and communication rate of wireless communication also change, and problems such as a case in which the communication rate required for transmitting image data cannot be ensured so moving image capturing cannot be performed are likely to occur.

The radiation imaging system disclosed in Japanese Patent Laid-Open No. 2018-7851 obtains the communication rate between the radiation imaging apparatus and the control apparatus, and enables moving image capturing if the communication rate is equal to or higher than a specified value.

However, in the radiation imaging system disclosed in Japanese Patent Laid-Open No. 2018-7851, an operator cannot recognize the margin in a communication state. Therefore, for example, when moving image capturing is selected in a state in which only the insufficient margin is left for the communication rate, there can be a case in which moving image capturing cannot be performed due to a slight decrease in communication rate.

The present invention has been made in consideration of the above problem, and provides a radiation imaging technique capable of displaying information indicating the margin in a communication state.

SUMMARY OF THE INVENTION

According to one aspect of the present invention, there is provided a radiation imaging system comprising a radiation imaging apparatus having a plurality of imaging modes, and a control apparatus configured to control imaging of a radiation image with respect to the radiation imaging apparatus, comprising: an obtaining unit configured to obtain information with respect to a communication state between the radiation imaging apparatus and the control apparatus; and a display control unit configured to cause a display unit of at least one of the radiation imaging apparatus and the control apparatus to display information indicating a margin in the communication state based on an imaging mode of the radiation imaging apparatus and the information with respect to the communication state.

According to another aspect of the present invention, there is provided a system comprising a portable terminal apparatus capable of playing image data, and a control apparatus configured to transmit image data to the portable terminal apparatus, comprising: an obtaining unit configured to obtain information with respect to a communication state between the portable terminal apparatus and the control apparatus; and a display control unit configured to cause a display unit of the portable terminal apparatus to display information indicating a margin in the communication state based on an image quality level of image data for playback and the information with respect to the communication state.

According to still another aspect of the present invention, there is provided a control method of a radiation imaging system comprising a radiation imaging apparatus having a plurality of imaging modes, and a control apparatus configured to control imaging of a radiation image with respect to the radiation imaging apparatus, comprising: obtaining information with respect to a communication state between the radiation imaging apparatus and the control apparatus; and causing a display unit of at least one of the radiation imaging apparatus and the control apparatus to display information indicating a margin in the communication state based on an imaging mode of the radiation imaging apparatus and the information with respect to the communication state.

According to yet another aspect of the present invention, there is provided a control method of a system comprising a portable terminal apparatus capable of playing image data, and a control apparatus configured to transmit image data to the portable terminal apparatus, comprising: obtaining information with respect to a communication state between the portable terminal apparatus and the control apparatus; and causing a display unit of the portable terminal apparatus to display information indicating a margin in the communication state based on an image quality level of image data for playback and the information with respect to the communication state.

According to the present invention, it becomes possible to display information indicating the margin in a communication state. By displaying the margin in the communication state, it becomes possible for an operator to grasp the reliability of communication, and convenience in imaging can be improved.

Further features of the present invention will become apparent from the following description of exemplary embodiments (with reference to the attached drawings).

BRIEF DESCRIPTION OF THE DRAWINGS

FIG. 5 is a table showing an example of minimum communication rates required for respective imaging modes in the first embodiment;

FIG. 6 is a view exemplarily showing a communication state level threshold table in the first embodiment;

FIG. 7 is a flowchart for explaining the procedure of communication state level display processing in the first embodiment;

FIG. 8 is a view showing an example of a communication state level threshold table in the second embodiment;

DESCRIPTION OF THE EMBODIMENTS

First Embodiment

Embodiments of the present invention will be exemplarily described in detail below with reference to the accompanying drawings. Note that the constituent elements described in the embodiments are merely examples. The technical scope of the present invention is determined by the scope of the appended claims and is not limited by the individual embodiments to be described below.

(Arrangement of Radiation Imaging System)

Figure 1:
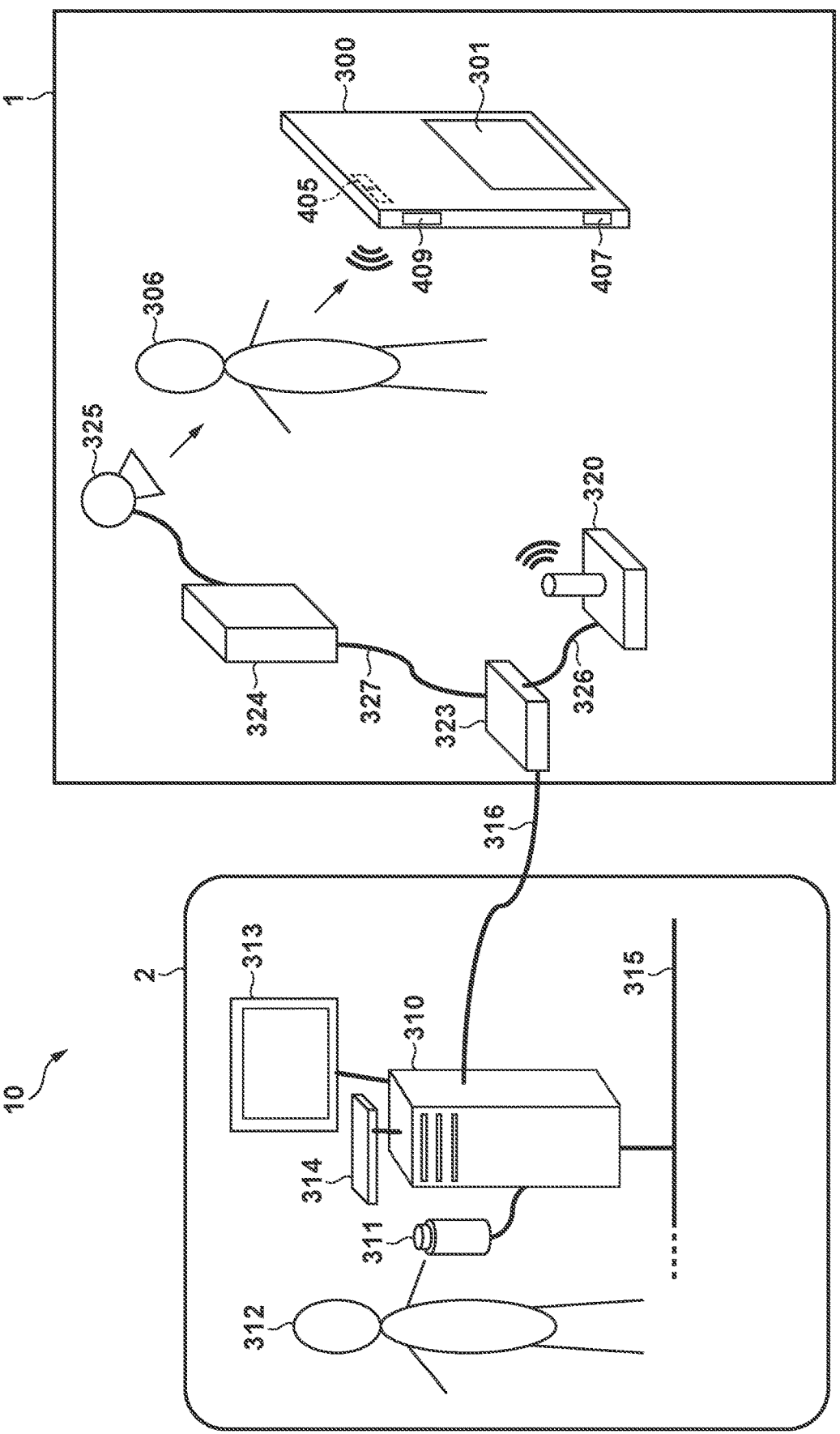
FIG. 1 is a view exemplarily showing a radiation imaging system in the first embodiment.

FIG. 1 is a view exemplarily showing a radiation imaging system according to the first embodiment. A radiation imaging system 10 includes a radiation imaging apparatus 300 having a plurality of imaging modes, and a control apparatus 310 that performs radiation image capturing control on the radiation imaging apparatus 300.

As shown in FIG. 1, the radiation imaging system 10 is provided in a radiation room 1 in which radiation imaging by radiation irradiation is performed and a control room 2 installed in the vicinity of the radiation room 1. In the radiation room 1, as the components of the radiation imaging system 10, a radiation imaging apparatus 300, an access point 320, a communication control apparatus 323, a radiation generation apparatus 324, and a radiation source 325 are provided. In the radiation room 1, a communication cable 326 that connects the access point 320 and the communication control apparatus 323, and a communication cable 327 that connects the communication control apparatus 323 and the radiation generation apparatus 324 are further provided.

In the control room 2, as the components of the radiation imaging system 10, a control apparatus 310, a radiation irradiation switch 311, a display device 313, an input device 314, a network 315 (in-hospital LAN), a communication cable 316 that connects the control apparatus 310 and the communication control apparatus 323 are provided.

The radiation imaging apparatus 300 includes a power supply control unit 301 formed by a battery or the like, a wireless communication unit 406, a wired communication unit 407, and an imaging apparatus display unit 409. The radiation imaging apparatus 300 has a plurality of imaging modes such as still image capturing and moving image capturing. Based on the selected imaging mode, the radiation imaging apparatus 300 detects radiation transmitted through a subject 306 and generates radiation image data.

The access point 320 performs wireless communication with the radiation imaging apparatus 300. In the radiation imaging system 10, the access point 320 is used to relay wireless communication between the radiation imaging apparatus 300 and the control apparatus 310.

The communication control apparatus 323 controls communication so that each of the access point 320, the radiation generation apparatus 324, and the control apparatus 310 can perform communication.

The radiation generation apparatus 324 controls the radiation source 325 so as to emit radiation based on a predetermined irradiation condition. The radiation source 325 irradiates the subject 306 with radiation in accordance with control by the radiation generation apparatus 324. The communication cable 326 is a cable for connecting the access point 320 and the communication control apparatus 323, and the communication cable 327 is a cable for connecting the radiation generation apparatus 324 and the communication control apparatus 323.

The control apparatus 310 communicates with the radiation generation apparatus 324 and the radiation imaging apparatus 300 via the communication control apparatus 323, and comprehensively controls the radiation imaging system 10.

The radiation irradiation switch 311 inputs a radiation irradiation timing in accordance with the operation by an operator 312. The input device 314 is a device that inputs an instruction from the operator 312, and is formed by various types of input devices such as a keyboard and a touch panel.

The display device 313 is a device that displays image-processed radiation image data and a GUI, and uses a display or the like. The network 315 (in-hospital LAN) is a network to which the control apparatus 310 is connected, and is, for example, an in-hospital backbone network. The communication cable 316 is a cable for connecting the control apparatus 310 and the communication control apparatus 323 in the radiation room 1.

Next, a still image capturing operation of the radiation imaging system 10 will be described. First, the operator 312 sets, in the control apparatus 310, subject information such as the identification information (ID), name, and date of birth of the subject 306, and imaging information such as the imaging portion and imaging direction of the subject 306. In addition to directly inputting the subject information and imaging information from the input device 314 and setting them in the control apparatus 310, the subject information and imaging information can be automatically set by selecting an examination order received via the network 315. The imaging information can also be set by selecting a preset imaging protocol.

After inputting the subject information, imaging information, imaging mode, and the like, the operator 312 adjusts the orientation of the subject 306 and the position of the radiation imaging apparatus 300. When the preparation for imaging is completed, the operator 312 presses the radiation irradiation switch 311. When the radiation irradiation switch 311 is pressed, radiation is emitted from the radiation source 325 toward the subject 306 and the subject 306 is irradiated with the radiation.

The radiation imaging apparatus 300 performs wireless communication with the radiation generation apparatus 324 to control the start and end of radiation irradiation. The radiation emitted toward the subject 306 is transmitted through the subject 306 and enters the radiation imaging apparatus 300. The radiation imaging apparatus 300 converts the incident radiation into visible light, and then detects it as a radiation image signal by a photoelectric conversion element. The radiation imaging apparatus 300 drives the photoelectric conversion element to read out the analog radiation image signal and converts the analog signal into a digital signal by an AD conversion circuit, thereby obtaining digital radiation image data (radiation image data). The obtained digital radiation image data (radiation image data) is transferred from the radiation imaging apparatus 300 to the control apparatus 310 by wireless communication.

In this embodiment, the control apparatus 310 also functions as an image processing apparatus and a display control apparatus. The control apparatus 310 performs image processing on the digital radiation image data (radiation image data) received from the radiation imaging apparatus 300, and causes the display device 313 to display a radiation image based on the image-processed radiation image data.

The above is the still image capturing operation in the radiation imaging system 10. Moving image capturing is implemented by repeating, within a specified time, the above-described still image capturing operation from radiation irradiation to displaying on the display device.

The radiation imaging apparatus 300 can perform imaging in a plurality of imaging modes different in field size, binning (resolution), sensitivity, frame rate, or the like in accordance with the imaging purposes.

FIG. 5 is a table showing an example of the imaging modes (combination of image size, binning, and frame rate) that can be set in the radiation imaging apparatus 300, and the lower limit values (minimum communication rates) of the communication rate required for imaging in the respective imaging modes. The minimum communication rate is set for each imaging mode, so that when any one of the plurality of imaging modes is selected, the minimum communication rate corresponding to the selected imaging mode can be obtained. For example, when moving image mode 1 is selected as the imaging mode, 250 Mbps is obtained as the minimum communication rate required at the time of imaging.

(Arrangement of Radiation Imaging Apparatus 300)

Figure 2:
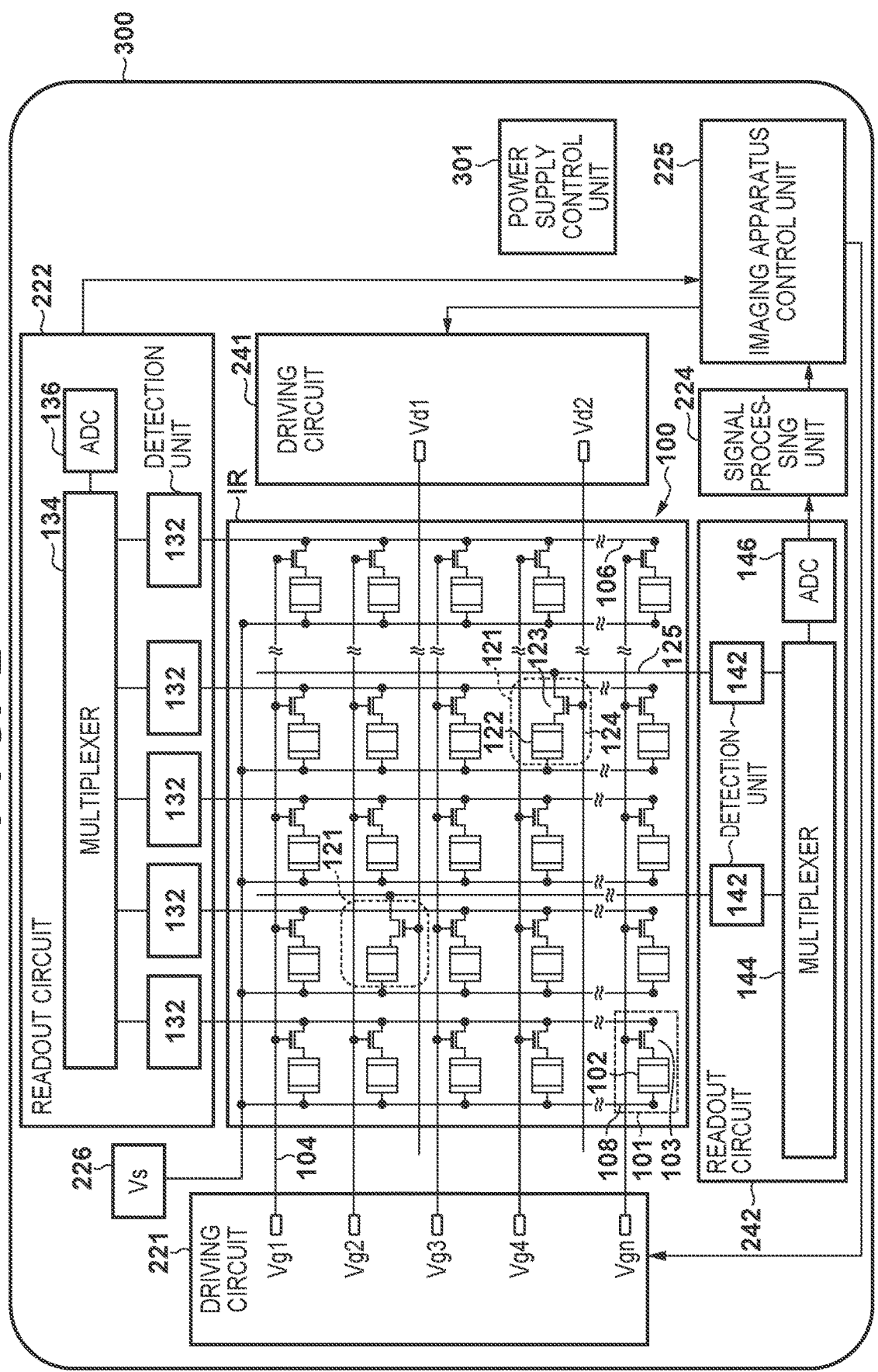
FIG. 2 is a view exemplarily showing the arrangement of a radiation imaging apparatus in the first embodiment.

FIG. 2 is a view exemplarily showing the arrangement of the radiation imaging apparatus 300. As shown in FIG. 2, the radiation imaging apparatus 300 includes a radiation detector 100 including a plurality of pixels arranged in an imaging region IR so as to form a plurality of rows and a plurality of columns. The radiation detector 100 has a function of detecting emitted radiation. That is, the radiation imaging apparatus 300 includes a plurality of imaging pixels 101 for obtaining a radiation image, and a detection pixel 121 for monitoring irradiation of radiation. The plurality of imaging modes of the radiation imaging apparatus include an AEC mode in which the start and stop of irradiation of the radiation are controlled based on the dose of the radiation monitored by the detection pixel.

As shown in FIG. 2, the imaging pixel 101 includes a first conversion element 102 that converts radiation into an electrical signal, and a first switch 103 arranged between a column signal line 106 and the first conversion element 102. The detection pixel 121 includes a second conversion element 122 that converts radiation into an electrical signal, and a second switch 123 arranged between a detection signal line 125 and the second conversion element 122. The detection pixel 121 is arranged in the same column as some of the plurality of imaging pixels 101.

Each of the first conversion element 102 and the second conversion element 122 is formed by a scintillator that converts radiation into light and a photoelectric conversion element that converts light into an electrical signal. The scintillator is generally formed in a sheet shape so as to cover the imaging region IR, and is shared by the plurality of pixels. Alternatively, each of the first conversion element 102 and the second conversion element 122 is formed by a conversion element that directly converts radiation into light.

Each of the first switch 103 and the second switch 123 includes, for example, a thin film transistor (TFT) with an active region formed by a semiconductor such as amorphous silicon or polysilicon (preferably, polysilicon).

The radiation imaging apparatus 300 includes the plurality of column signal lines 106 and a plurality of driving lines 104. Each column signal line 106 corresponds to one of the plurality of columns in the imaging region IR. Each driving line 104 corresponds to one of the plurality of rows in the imaging region IR. Each driving line 104 is driven by a driving circuit 221.

The first electrode of the first conversion element 102 is connected to the first main electrode of the first switch 103, and the second electrode of the first conversion element 102 is connected to a bias line 108. Here, one bias line 108 extends in the column direction and is commonly connected to the second electrodes of the plurality of first conversion elements 102 arranged in the column direction.

The bias line 108 receives a bias voltage Vs from an element power supply circuit 226. The bias voltage Vs is supplied from the element power supply circuit 226. The power supply control unit 301 is formed by a battery, a DCDC converter, or the like. The power supply control unit 301 includes the element power supply circuit 226, and forms a power supply for an analog circuit and a power supply for a digital circuit that performs drive control, wireless communication, and the like.

The second main electrodes of the first switches 103 of the plurality of imaging pixels 101 forming one column are connected to one column signal line 106. The control electrodes of the first switches 103 of the plurality of imaging pixels 101 forming one row are connected to one driving line 104. The plurality of column signal lines 106 are connected to a readout circuit 222. Here, the readout circuit 222 includes a plurality of detection units 132, a multiplexer 134, and an analog/digital converter (to be referred to as an AD converter hereinafter) 136. Each of the plurality of column signal lines 106 is connected to the corresponding detection unit 132 among the plurality of detection units 132 of the readout circuit 222. Here, one column signal line 106 corresponds to one detection unit 132. The detection unit 132 includes, for example, a differential amplifier. The multiplexer 134 selects the plurality of detection units 132 in a predetermined order, and supplies a signal from the selected detection unit 132 to the AD converter 136. The AD converter 136 converts the supplied signal into a digital signal and outputs the digital signal to an imaging apparatus control unit 225.

The first electrode of the second conversion element 122 is connected to the first main electrode of the second switch 123, and the second electrode of the second conversion element 122 is connected to the bias line 108. The second main electrode of the second switch 123 is connected to the detection signal line 125. The control electrode of the second switch 123 is electrically connected to a driving line 124.

The radiation imaging apparatus 300 includes the plurality of detection signal lines 125. One or the plurality of detection pixels 121 are connected to one detection signal line 125. The driving line 124 is driven by a driving circuit 241. One or the plurality of detection pixels 121 are connected to one driving line 124. The detection signal line 125 is connected to a readout circuit 242. Here, the readout circuit 242 includes a plurality of detection units 142, a multiplexer 144, and an AD converter 146. Each of the plurality of detection signal lines 125 is connected to the corresponding detection unit 142 among the plurality of detection units 142 of the readout circuit 242. Here, one detection signal line 125 corresponds to one detection unit 142. The detection unit 142 includes, for example, a differential amplifier. The multiplexer 144 selects the plurality of detection units 142 in a predetermined order, and supplies a signal from the selected detection unit 142 to the AD converter 146.

The AD converter 146 converts the supplied signal into a digital signal and outputs the digital signal. The output of the readout circuit 242 (AD converter 146) is supplied to a signal processing unit 224 and processed by the signal processing unit 224. The signal processing unit 224 outputs information indicating radiation irradiation with respect to the radiation imaging apparatus 300 to the imaging apparatus control unit 225 based on the output of the readout circuit 242 (AD converter 146). More specifically, for example, the signal processing unit 224 can detect radiation irradiation with respect to the radiation imaging apparatus 300 and calculate the radiation irradiation amount and/or the cumulative irradiation amount.

The imaging apparatus control unit 225 controls the driving circuits 221 and 241, the readout circuits 222 and 242, and the like based on information from the readout circuit 222 (AD converter 136), information from the signal processing unit 224, and a control command from the control apparatus 310.

(Explanation of Operation in Dose Control)

Next, an operation in dose control performed using the radiation imaging apparatus 300 will be described. The operator 312 inputs the radiation irradiation conditions (for example, dose, maximum irradiation time, tube current, tube voltage, and the like), the radiation detection region (ROI) where the radiation is to be monitored, the portion information, and the like to the control apparatus 310. The control apparatus 310 transmits the input radiation irradiation conditions, radiation detection region (ROI), portion information, and the like to the radiation imaging apparatus 300 and the radiation generation apparatus 324. When the preparation for imaging is completed and the operator 312 presses the radiation irradiation switch 311, radiation is emitted. The emitted radiation is transmitted through the subject 306 and enters the radiation imaging apparatus 300. The radiation imaging apparatus 300 detects the radiation incident on the radiation detection region (ROI) by the detection pixel 121, and the signal processing unit 224 calculates, based on the signal detected by the detection pixel 121, an integrated irradiation amount that is an integrated value of the doses (arrival doses) detected in a predetermined period. Here, the imaging apparatus control unit 225 calculates an appropriate dose from the integrated irradiation amount information from the signal processing unit 224 and the portion information and imaging information input by the operator 312, and determines a radiation irradiation stop timing. The radiation imaging apparatus 300 notifies the radiation generation apparatus 324 of the stop by wireless communication based on the determined radiation irradiation stop timing. The radiation generation apparatus 324 stops the radiation irradiation based on the radiation irradiation stop timing notified from the radiation imaging apparatus 300.

Note that the radiation imaging apparatus 300 notifies the stop of radiation irradiation as a result of detecting the radiation, but the present invention is not limited to this. The radiation imaging apparatus 300 may transmit the arrival dose every predetermined time as a detection result, and the radiation generation apparatus 324 may calculate an integrated value of the arrival doses.

(Functional Arrangement of Imaging Apparatus Control Unit 225)

Figure 3:
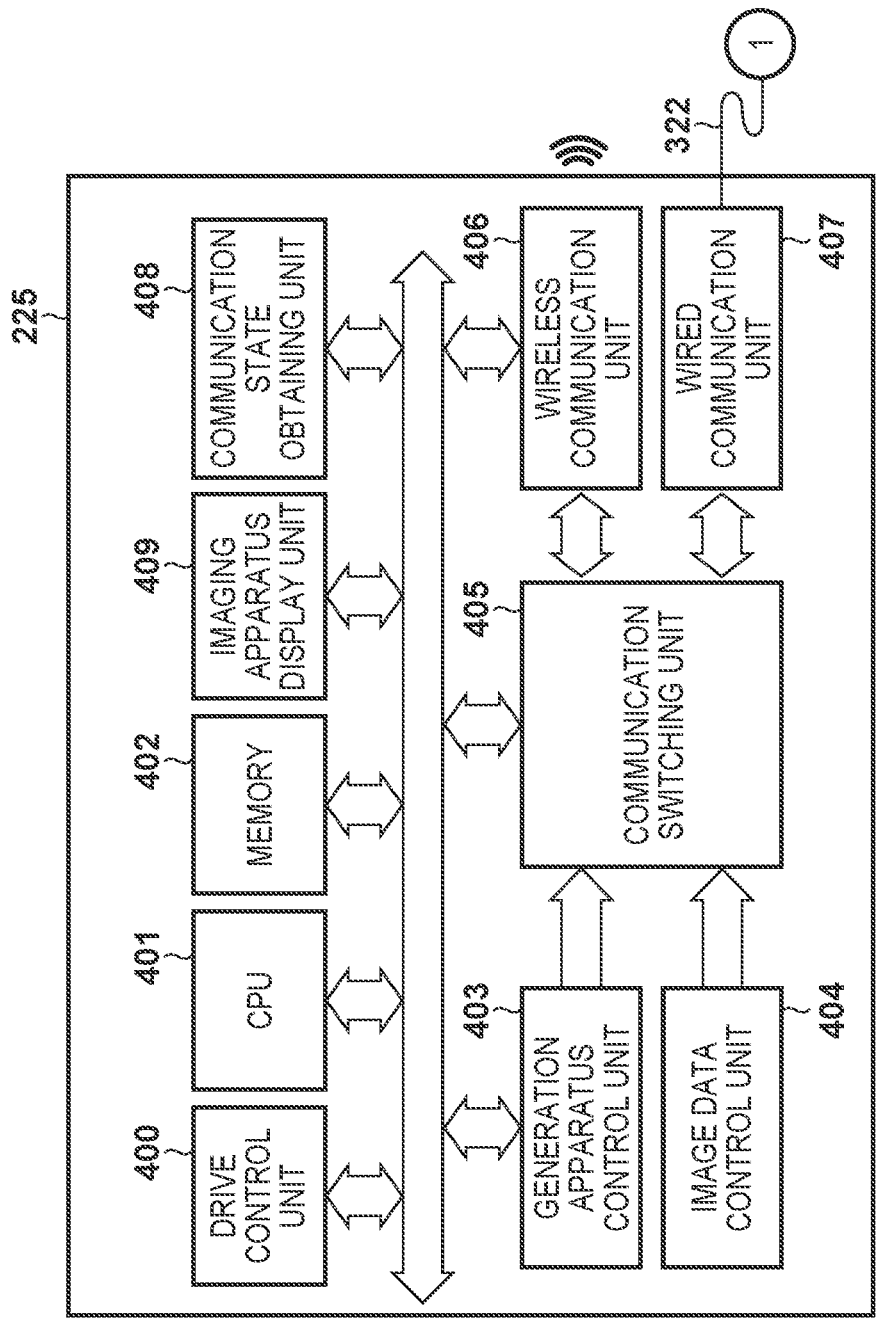
FIG. 3 is a view showing the functional arrangement of an imaging apparatus control unit of the radiation imaging apparatus in the first embodiment.

FIG. 3 is a view showing the functional arrangement of the imaging apparatus control unit 225 of the radiation imaging apparatus 300. As shown in FIG. 3, the imaging apparatus control unit 225 includes a drive control unit 400, a CPU 401, a memory 402, a generation apparatus control unit 403, an image data control unit 404, a communication switching unit 405, the wireless communication unit 406, the wired communication unit 407, a communication state obtaining unit 408, and the imaging apparatus display unit 409.

The drive control unit 400 controls the driving circuits 221 and 241 and the readout circuits 222 and 242 based on information from the readout circuit 222 (AD converter 136), information from the signal processing unit 224, and a command from the control apparatus 310. The CPU 401 performs overall control of the radiation imaging apparatus 300 using programs and various types of data stored in the memory 402. The memory 402 stores, for example, programs and various types of data used when the CPU 401 executes processing. Further, the memory 402 stores various types of data obtained from processing by the CPU 401, and radiation image data.

The generation apparatus control unit 403 controls communication with the radiation generation apparatus 324 based on information from the signal processing unit 224, a command from the control apparatus 310, and information from the drive control unit 400. The generation apparatus control unit 403 exchanges information (for example, a notification of a start/end of radiation irradiation, a radiation irradiation amount, an integrated irradiation amount, or the like) regarding control of the radiation generation apparatus 324 with the radiation generation apparatus 324.

The image data control unit 404 stores image data from the readout circuit 222 in the memory 402 and controls communication with the control apparatus 310. The image data control unit 404 exchanges radiation image data and control-related information (for example, a control command and the like) with the control apparatus 310.

In the radiation imaging system 10, communication between the radiation imaging apparatus 300 and the control apparatus 310 is wireless communication or wired communication. The communication switching unit 405 switches the communication units (wireless communication unit 406 and wired communication unit 407) so as to enable communication by the wired communication unit 407 when a cable 322 is connected to the radiation imaging apparatus 300, and enable communication by the wireless communication unit 406 when the cable 322 is disconnected from the radiation imaging apparatus 300. The wireless communication unit 406 communicates with the communication control apparatus 323 via the access point 320. The wired communication unit 407 communicates with the communication control apparatus 323 via the cable 322.

The communication state obtaining unit 408 obtains information with respect to the communication state between the radiation imaging apparatus 300 and the control apparatus 310 from the wireless communication unit 406 or the wired communication unit 407.

The imaging apparatus display unit 409 displays the state of the imaging apparatus, the remaining battery level, the communication state obtained by the communication state obtaining unit 408, and the like.

(Functional Arrangements of Communication Control Apparatus 323 and Control Apparatus 310)

Figure 4:
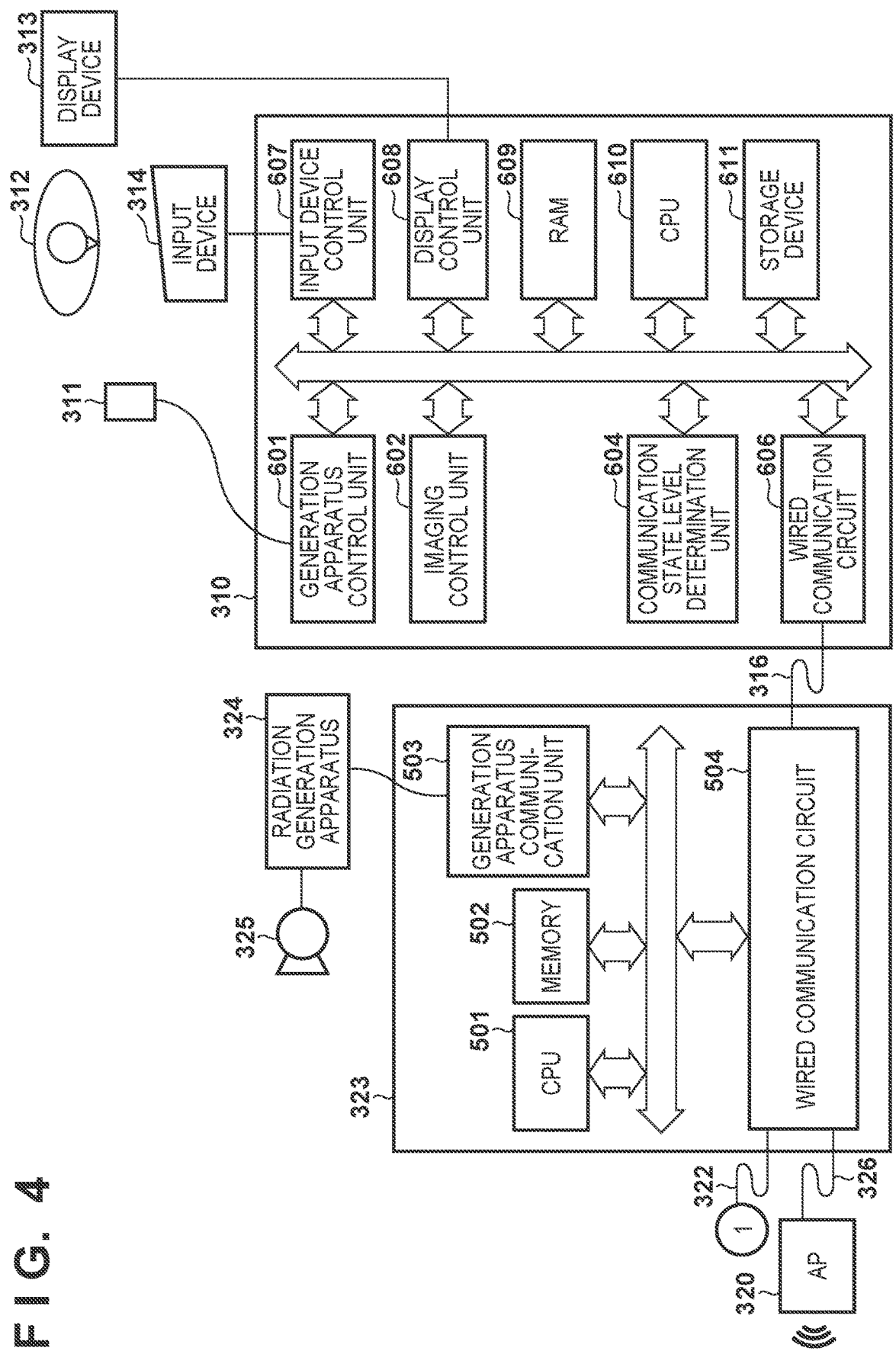
FIG. 4 is a view exemplarily showing the functional arrangements of a communication control apparatus and a control apparatus in the first embodiment.

FIG. 4 is a view exemplarily showing the functional arrangements of the communication control apparatus 323 and the control apparatus 310. The communication control apparatus 323 includes a CPU 501, a memory 502, a generation apparatus communication unit 503, and a wired communication circuit 504. In the communication control apparatus 323, the CPU 501 performs overall control of the communication control apparatus 323 using programs and various types of data stored in the memory 502.

The memory 502 stores, for example, programs and various types of data used when the CPU 501 executes processing. Further, the memory 502 stores various types of data obtained from processing by the CPU 501, and communication data.

The generation apparatus communication unit 503 communicates with the radiation generation apparatus 324 based on an instruction from a generation apparatus control unit 601 of the control apparatus 310 and an instruction from the generation apparatus control unit 403 of the radiation imaging apparatus 300. The wired communication circuit 504 has a switching HUB function, for example, and enables wired communication with each of the access point 320, the radiation imaging apparatus 300 when connected by wire, and the control apparatus 310.

The control apparatus 310 includes the generation apparatus control unit 601, an imaging control unit 602, a wired communication circuit 606, an input device control unit 607, a display control unit 608, a RAM 609, a CPU 610, a storage device 611, and a communication state level determination unit 604.

In the control apparatus 310, the generation apparatus control unit 601 performs control related to radiation generation by the radiation generation apparatus 324 based on an imaging instruction from the operator 312. The imaging control unit 602 performs control related to radiation imaging with respect to the radiation imaging apparatus 300 based on an imaging instruction from the operator 312.

The wired communication circuit 606 is responsible for communication of various types of data and various types of information between the control apparatus 310 and the communication control apparatus 323. The input device control unit 607 performs various types of control operations related to the input device 314 such as switching the display of the input device 314 in accordance with the operation of the input device 314 by the operator 312.

The RAM 609 temporarily stores various types of data and various types of information required for processing by the control apparatus 310. The CPU 610 performs overall control of the control apparatus 310 using programs and various types of data stored in the RAM 609. The storage device 611 is formed by an external storage device such as a hard disk, for example, and stores various types of programs, various types of data, various types of information, or the like.

The communication state level determination unit 604 determines the communication state level based on the information with respect to the communication state and the selected imaging mode. The communication state level determination unit 604 holds a threshold table in which a threshold of the information with respect to the communication state for the communication state level is set for each of the plurality of imaging modes, and determines the communication state level from the threshold table based on the information with respect to the communication state and the imaging mode. That is, the communication state level is determined based on the information (for example, communication rate) indicating the communication state obtained by the communication state obtaining unit 408 of the imaging apparatus control unit 225 in the radiation imaging apparatus 300 and the selected imaging mode.

The display control unit 608 performs various types of control operations related to the display of the display device 313, and performs display control for causing the display device 313 to display the communication state level determined by the communication state level determination unit 604 as the information indicating the margin. The display control unit 608 can change the display of the information indicating the margin based on comparison between the threshold of the information with respect to the communication state required for communication (for example, the threshold of communication rate) set for each imaging mode and the obtained information with respect to the communication state, and cause the display device 313 to display the change display.

For example, the display control unit 608 can cause the display device 313 to display a numerical value corresponding to the determined communication state level as the information indicating the margin, or cause the display device 313 to display a graphic pattern corresponding to the determined communication state level (a graphic pattern of one or more antennas corresponding to the determined communication state level) as the information indicating the margin.

In addition, the display control unit 608 can change the graphic pattern in accordance with the communication state level and cause the display device 313 to display the changed graphic pattern, or change the display color of the graphic pattern in accordance with the communication state level and cause the display device 313 to display the graphic pattern with the changed display color.

(Communication State Level Display Processing)

Next, the procedure of communication state level display processing will be described with reference to the flowchart shown in FIG. 7. When the radiation imaging system 10 is activated, the wireless communication unit 406 of the radiation imaging apparatus 300 establishes wireless communication with the access point 320 in step S71.

In step S72, the communication state obtaining unit 408 of the radiation imaging apparatus 300 obtains information with respect to the communication state from the wireless communication unit 406. The obtained information with respect to the communication state is transmitted to the communication state level determination unit 604 of the control apparatus 310. For example, when the communication rate between the wireless communication unit 406 and the access point 320 is 300 Mbps, the communication state obtaining unit 408 obtains, from the wireless communication unit 406, a communication rate of 300 Mbps as the information with respect to the communication state and transmits it to the communication state level determination unit 604.

In step S73, the communication state level determination unit 604 of the control apparatus 310 selects the values of "standard (imaging mode unselected)" as thresholds from a communication state level threshold table. FIG. 6 is a view showing an example of the communication state level threshold table. Since the imaging mode has not been selected at the time of step S73, the values in the column of "standard (imaging mode unselected)" are used as the thresholds of the threshold table.

In step S74, the communication state level determination unit 604 of the control apparatus 310 determines the communication state level from the information with respect to the communication state received from the radiation imaging apparatus 300 using the thresholds obtained in step S73, and the display control unit 608 performs display control so that the determined communication state level is displayed on the display device 313 as the information indicating the margin.

The display control unit 608 performs display control so that the determined communication state level is displayed on the display device 313 as the information indicating the margin. The communication state level may be displayed using a number, or a graphic pattern (icon) indicating the communication state in accordance with the communication state level. For example, when the information with respect to the communication state (communication rate) obtained in step S72 is 300 Mbps, the communication state level determination unit 604 refers to "standard (imaging mode unselected)" in the threshold table shown in FIG. 6, and obtains communication state level "5" corresponding to the communication rate of 300 Mbps. When the communication state level is "5", the display control unit 608 displays a graphic pattern (icon) of five antennas in the "antenna display" column shown in FIG. 6. As the display of the communication state level, the display of a graphic pattern of antenna is illustrative, and various types of visually recognizable graphic patterns (icons), numerical values, or the like can be used. For example, a graphic pattern (icon) and a numerical value may be displayed in combination.

If one imaging mode is selected from the plurality of imaging modes via the input device 314 by the operator 312 in step S75 (YES in step S75), the process advances to step S76. On the other hand, if no imaging mode is selected (NO in step S75), the process returns to step S72, and the processing from step S72 to step S75 is repeated until one imaging mode is selected. Here, the input device 314 functions as a selection unit used for selecting one imaging mode from the plurality of imaging modes.

In step S76, the communication state obtaining unit 408 of the radiation imaging apparatus 300 obtains the information with respect to the communication state as in step S72, and transmits the obtained information with respect to the communication state to the communication state level determination unit 604 of the control apparatus 310.

In step S77, the communication state level determination unit 604 obtains, based on the selected imaging mode, the thresholds of the selected imaging mode from the communication state level threshold table.

The communication state level thresholds shown in FIG. 6 are set for each imaging mode based on the communication rate required for performing communication. For example, the lower limit value (minimum communication rate) of the communication rate required for imaging in each imaging mode shown in FIG. 5 is set as the lowest threshold of communication state level "4". By setting the threshold in this manner, regardless of which imaging mode is selected, it is possible to indicate that imaging can be performed as long as the communication state level is "4" or higher (the antenna display of four or more antennas). If the communication state level is "5" (the antenna display of five antennas), it is possible to indicate that the communication environment (communication rate) has a sufficient margin for the selected imaging mode. Note that in still image AEC imaging, since radiation irradiation start/stop control needs to be performed with a minimum delay, the thresholds are different from those in normal still image capturing, but set at the same level as moving image mode 1.

In step S78, the communication state level determination unit 604 of the control apparatus 310 determines the communication state level based on the thresholds obtained in step S77 and the information with respect to the communication state received from the radiation imaging apparatus 300. The display control unit 608 performs display control so that the determined communication state level is displayed on the display device 313 as the information indicating the margin. For example, when the information with respect to the communication state (communication rate) obtained in step S76 is 300 Mbps and the imaging mode selected in step S75 is moving image mode 1, the communication state level determination unit 604 obtains communication state level "4" corresponding to the communication rate of 300 Mbps with reference to moving image mode 1 in the threshold table shown in FIG. 6. For example, when the communication state level is "4", the display control unit 608 performs display control so that the graphic pattern (icon) of four antennas in the "antenna display" column shown in FIG. 6 is displayed on the display device 313. That is, based on the selected imaging mode (step S75), the display control unit 608 changes the information indicating the margin (changes the graphic pattern of five antennas to the graphic pattern of four antennas), and causes the display device 313 to display the changed information.

The display control unit 608 can perform display control so that a notation of imaging mode is displayed in the vicinity of the displayed antenna graphic pattern (icon). By displaying the notation of imaging mode in the vicinity of the antenna graphic pattern (icon) in this manner, the operator can visually recognize the communication state and the imaging mode, and can easily grasp the situation. The processing from step S75 to step S78 is repeatedly executed until the imaging mode is changed.

According to the radiation imaging system 10 in the first embodiment, by displaying the communication state level using the threshold determined based on the selected imaging mode, information indicating the margin in the communication state can be displayed regardless of which imaging mode is selected. Therefore, the operator can grasp the reliability of communication, and convenience can be improved.

Note that in the first embodiment, a communication rate is used as information with respect to a communication state, but the information is not limited to this. For example, a signal to noise ratio (SNR) or a received signal strength indicator (RSSI) may be measured and used as a communication parameter. That is, the communication state obtaining unit 408 obtains the communication parameter in the communication between the radiation imaging apparatus 300 and the control apparatus 310. The communication parameter includes at least one of a communication rate, a signal to noise ratio (SNR), a received signal strength indicator (RSSI), and a communication delay time in the communication. The communication state level determination unit 604 may determine the communication state level using at least one of these values.

For example, in moving image mode 2, the communication state level determination unit 604 may determine that the communication state level is "5" when the SNR is equal to or higher than 60 dBm, and the communication state level is "1" when the SNR is lower than 20 dBm. Alternatively, the communication state level determination unit 604 may determine that the communication state level is "5" when the RSSI is equal to or higher than −20 dBm, and the communication state level is "1" when the RSSI is equal to or lower than −60 dBm.

Further, the communication state level determination unit 604 may measure, as the information indication the communication state, a communication delay time from the transmission of a response time measurement packet from the communication state obtaining unit 408 to the control apparatus 310 to the arrival of the response from the control apparatus 310, and determine the communication state level based on the communication delay time.

Since the communication state can vary, the communication state obtaining unit 408 obtains pieces of the information with respect to the communication state through a plurality of times of communication, and sets, as a representative value of the information with respect to the communication state, a statistical value (for example, a maximum value, an average value, or a mode value) obtained from the obtained pieces of information with respect to the communication state. The communication state level determination unit 604 determines the communication state level based on the set representative value of the information with respect to the communication state and the imaging mode of the radiation imaging apparatus 300.

The display control unit 608 causes the display device 313 to display, as the information indicating the margin in the communication state, the communication state level determined based on the set representative value of the information with respect to the communication state and the imaging mode of the radiation imaging apparatus 300.

In the radiation imaging system 10 according to the first embodiment, the communication state levels are expressed as six levels (0 to 5). However, the number of levels may be smaller or larger depending on the requirements of the system.

Further, the antenna display may be displayed using a numerical value such as 0 to 100. More specifically, the obtained communication rate may be multiplied by a coefficient and displayed so that the display becomes a predetermined value (for example, 50) at the communication rate required for each imaging mode.

Furthermore, in the radiation imaging system 10 according to the first embodiment, the arrangement in which wireless communication is performed has been taken as an example, but the present invention is not limited to this, and the radiation imaging apparatus 300 and the communication control apparatus 323 may be connected by wired communication. In the case of wired connection, it is possible to obtain the communication rate or link information from the wired communication unit 407 or measure the communication delay time, and display the communication state level using a threshold table.

Second Embodiment

The second embodiment will be described next. In the first embodiment, there has been described the arrangement in which the communication state level is determined based on the information (for example, the communication rate or the like) indicating the communication state and the imaging mode, and the determined communication state level is displayed as the information indicating the margin. However, in the second embodiment, there will be described an arrangement in which the information indicating the margin is identifiably displayed using color information based on the determined communication state level.

The arrangement of a radiation imaging system 10 is similar to that described in the first embodiment, and portions different from the first embodiment will be described in the following description.

FIG. 8 is a view showing an example of a communication state level threshold table according to the second embodiment. The flowchart for explaining the procedure of communication state level display processing is similar to that in the first embodiment. Therefore, the procedure of communication state level display processing in the second embodiment will be described using FIG. 7.

After the radiation imaging system 10 is activated, the processing from step S71 to step S76 is similar to that in the first embodiment.

In step S77, a communication state level determination unit 604 obtains, based on the selected imaging mode, the thresholds of the selected imaging mode from the communication state level threshold table shown in FIG. 8. The communication state level thresholds shown in FIG. 8 are set for each imaging mode based on the communication rate required for performing communication, as in FIG. 6. Different display colors are set corresponding to different communication state levels. For example, a yellowish green display indicates a state in which the required communication rate is ensured (the communication state level is "4"), and a green display indicates a state in which there is a sufficient margin (the communication state level is "5").

In step S78, the communication state level determination unit 604 of a control apparatus 310 determines the communication state level based on the thresholds obtained in step S77 and the information with respect to the communication state received from a radiation imaging apparatus 300. A display control unit 608 causes a display device 313 to display the communication state while using the threshold obtained in step S73 for the number of antennas to be displayed and using the antenna display color set for each communication state level shown in FIG. 8. For example, when the information (for example, communication rate) indicating the communication state obtained in step S76 is 100 Mbps and the imaging mode selected in step S75 is "still image", the communication state level determination unit 604 refers to "standard" in the threshold table shown in FIG. 6 (step S73) and obtains communication state level "2" corresponding to the communication rate of 100 Mbps. A graphic pattern of two antennas is displayed by the display control unit 608 based on the threshold for "standard" in FIG. 6.

Next, the communication state level determination unit 604 refers to "still image" in the threshold table shown in FIG. 8 (step S77) and obtains communication state level "5" corresponding to the communication rate of 100 Mbps. Since the communication rate is as low as 100 Mbps, the number of antennas to be displayed is small (two antennas), but the low communication rate is enough when the selected imaging mode is "still image". Therefore, the antenna display color used by the display control unit 608 is set to green (sufficient margin) corresponding to communication state level "5" based on the threshold for "still image" in FIG. 8.

According to the radiation imaging system 10 in the second embodiment, it is possible to display the communication state (a graphic pattern of one or more antennas) in a standard communication mode (for example, "standard") while displaying the communication state level (the communication margin in the communication environment) using the color corresponding to the selected imaging mode.

That is, the display control unit 608 performs display control of causing the display unit to display a graphic pattern (one or more antennas) as the display of the information indicating the margin in a standard imaging mode (for example, "standard"), and changing the display color of the graphic pattern as the display of the information indicating the margin in the selected imaging mode. With the display control as described above, not only the communication margin in the communication environment in the selected imaging mode can be visually grasped, but also the standard communication environment regardless of the selected imaging mode can be grasped from the number of antennas.

Note that in each of the first and second embodiments, there has been described the arrangement in which the display control unit 608 of the control apparatus 310 causes the display device 313 to display the communication state level determined by the communication state level determination unit 604 as the information indicating the margin, but the information indicating the margin may be displayed on the radiation imaging apparatus 300 side. That is, it is also possible that the control apparatus 310 transmits the information with respect to the communication state level to the radiation imaging apparatus 300, and the CPU 401 of the radiation imaging apparatus 300 functions as a display control unit and performs display control so that the transmitted communication state level is displayed as the information indicating the margin on an imaging apparatus display unit 409. The display control unit 608 of the control apparatus 310 and the CPU 401 (display control unit) of the radiation imaging apparatus 300 cause the display device (display device 313 or the imaging apparatus display unit 409) of at least one of the radiation imaging apparatus 300 and the control apparatus 310 to display the information indicating the margin in the communication state based on the imaging mode of the radiation imaging apparatus 300 and the information with respect to the communication state.

In addition, a communication state obtaining unit 408 may be arranged in the control apparatus 310, and the communication state obtaining unit 408 in the control apparatus 310 may obtain the communication state from an access point 320 or a wired communication circuit 504.

Third Embodiment

The third embodiment will be described next. In each of the first and second embodiments, there has been described the example of displaying the information indicating the margin in the communication state at the time of transmitting image data obtained by imaging from the radiation imaging apparatus 300 to the control apparatus 310. In the third embodiment, there will be described the arrangement of a system that displays the communication state at the time of playing, by a portable terminal apparatus such as a smartphone or a tablet PC, a radiation image (image data) stored in a control apparatus 310.

Figure 9:
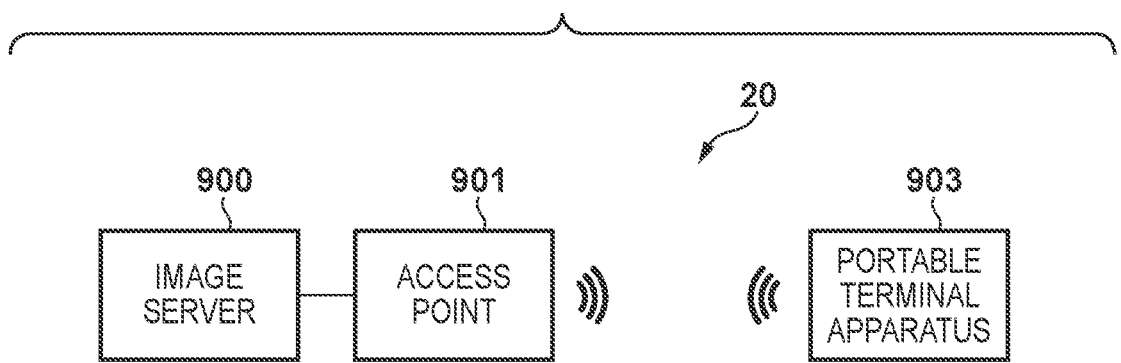
FIG. 9 is a view showing a radiation imaging system in the third embodiment.

FIG. 9 is a view showing an arrangement example of a radiation imaging system 20 (image playback system) as the system according to the third embodiment. As shown in FIG. 9, the radiation imaging system 20 includes a portable terminal apparatus 903, an access point 901, and an image server 900 (control apparatus 310). The functional arrangement of the image server 900 (control apparatus 310) is similar to that of the control apparatus 310 described with reference to FIG. 4.

The portable terminal apparatus 903 is, for example, a smartphone, tablet PC, or the like, and performs wireless communication with the image server 900 via the access point 901. In addition, the portable terminal apparatus 903 can play image data received from the image server 900. The image server 900 transmits image data obtained by imaging in the radiation imaging apparatus 300 to the portable terminal apparatus 903.

In the radiation imaging system 20, the access point 901 is used to relay communication between the image server 900 and the portable terminal apparatus 903. The image server 900 (control apparatus 310) holds image data obtained by imaging in the radiation imaging apparatus 300, and transmits a radiation image (image data) for playback to the portable terminal apparatus 903 when receiving a request from the portable terminal apparatus 903.

Figure 10:
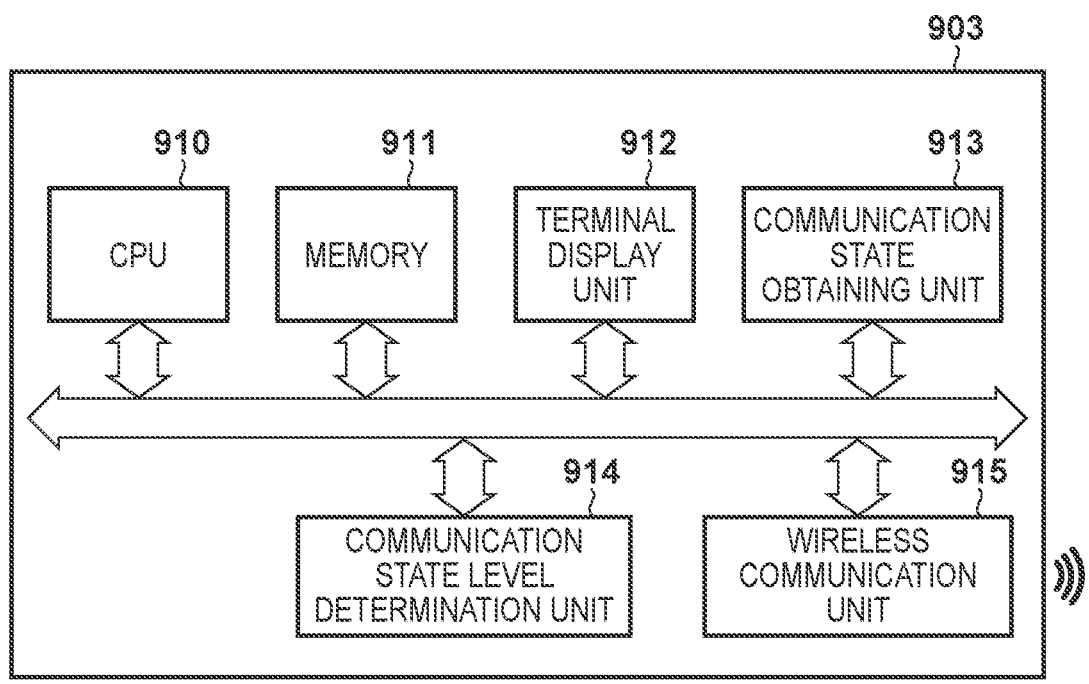
FIG. 10 is a view showing a portable terminal apparatus in the third embodiment.

FIG. 10 is a view exemplarily showing the functional arrangement of the portable terminal apparatus 903. As shown in FIG. 10, the portable terminal apparatus 903 includes a CPU 910, a memory 911, a terminal display unit 912, a communication state obtaining unit 913, a communication state level determination unit 914, and a wireless communication unit 915.

The CPU 910 performs overall control of the portable terminal apparatus 903 using programs and various types of data stored in the memory 911. The memory 911 stores, for example, programs and various types of data used when the CPU 910 executes processing. Further, the memory 911 stores various types of data obtained from processing by the CPU 910, and a radiation image (image data) for playback.

The terminal display unit 912 displays image data, the communication state obtained by the communication state obtaining unit 913, and the like. The communication state obtaining unit 913 obtains information with respect to the communication state between the portable terminal apparatus 903 and the image server 900 from the wireless communication unit 915.

The communication state level determination unit 914 holds the imaging mode information of the image data for playback stored in the image server 900, and a table showing the communication state level thresholds for each imaging mode, and determines the communication state level based on the information (for example, communication rate) indicating the communication state obtained by the communication state obtaining unit 913 and the imaging mode of the selected image data for playback. The wireless communication unit 915 communicates with the image server 900 via the access point 901.

Next, the operation of the radiation imaging system 20 will be described. A communication state level threshold table will be described using FIGS. 6 and 8, and the procedure of communication state level display processing will be described using the flowchart shown in FIG. 7. After the radiation imaging system 20 is activated, the processing from step S71 to step S74 is similar to that in the second embodiment.

In step S75, the image data for playback stored in the image server 900 (control apparatus 310) is selected using the portable terminal apparatus 903. Since the communication state level determination unit 914 stores the imaging mode information of the image data for playback, it is possible to determine (select), by selecting the image data for playback, the imaging mode corresponding to the selected image data for playback.

In step S76, the communication state obtaining unit 913 obtains the information with respect to the communication state as in step S72, and transmits the obtained information with respect to the communication state to the communication state level determination unit 914.

In step S77, the communication state level determination unit 914 obtains the thresholds of the imaging mode corresponding to the selected image data for playback from the communication state level threshold table shown in FIG. 8.

In step S78, the communication state level determination unit 914 determines the communication state level based on the thresholds of the imaging mode obtained in step S77 and the information with respect to the communication state obtained in step S76. As for a graphic pattern of one or more antennas, the communication state level determination unit 914 uses the threshold obtained with reference to "standard" in the threshold table shown in FIG. 6 (step S73). As for a display color of the graphic pattern of one or more antennas, the communication state level determination unit 914 uses the threshold set in the threshold table shown in FIG. 8. The CPU 910 of the portable terminal apparatus 903 functions as a display control unit. The CPU 910 (display control unit) causes the terminal display unit 912 of the portable terminal apparatus 903 to display the information indicating the margin in the communication state based on the imaging mode of the image data for playback and the information with respect to the communication state. That is, the CPU 910 (display control unit) performs display control of causing the terminal display unit 912 to display a graphic pattern (one or more antennas) as the display of the information indicating the margin in a standard imaging mode, and changing the display color of the graphic pattern as the display of the information indicating the margin in the selected imaging mode.

For example, when the information (communication rate) indicating the communication state obtained in step S76 is 100 Mbps and the imaging mode of the image data for playback selected in step S75 is moving image mode 2, the communication state level determination unit 914 refers to "standard" in the threshold table shown in FIG. 6 (step S73) and obtains communication state level "2" corresponding to the communication rate of 100 Mbps. A graphic pattern of two antennas is displayed based on the threshold for "standard" in FIG. 6.

Next, the communication state level determination unit 914 refers to "moving image mode 2" in the threshold table shown in FIG. 8 (step S77) and obtains communication state level "4" corresponding to the communication rate of 100 Mbps. Since the communication rate is as low as 100 Mbps, the number of antennas to be displayed is small, but the communication rate may not be so high when the selected imaging mode is "moving image mode 2". Therefore, the antenna display color is set to yellowish green (a state in which the communication rate is ensured) corresponding to communication state level "4" based on the threshold for "moving image mode 2" in FIG. 8.

According to the radiation imaging system 20 in the third embodiment, regardless of the imaging mode of the image data selected to be played, it is possible to display the information indicating the margin in communication for the imaging mode corresponding to the selected image data in the communication environment in a visually graspable manner. Therefore, the operator can grasp the reliability of communication, and convenience can be improved.

Note that in the third embodiment, the threshold is determined based on the imaging mode of the image data for playback. However, thresholds may be set for each image quality level (high image quality, standard image quality, low image quality, or the like) upon playing the image data for playback, and the communication state level may be determined using these thresholds. That is, the CPU 910 (display control unit) can cause the terminal display unit 912 of the portable terminal apparatus 903 to display the information indicating the margin in the communication state based on the image quality level of the image data for playback and the information with respect to the communication state. Even in this case, it is possible to display whether the image can be played in the selected image quality in the current wireless communication environment without stopping the playback, and the remaining margin. Therefore, the operator can grasp the reliability of communication, and convenience can be improved.

In the third embodiment, as in the first embodiment, the communication state level threshold may be changed and displayed for each imaging mode. Further, the display color in the antenna display is used as a method for identifying the margin in communication in the second and third embodiments, but the present invention is not limited to this. The magnitude of the communication state level may be identified using shading.

The embodiments (first to third embodiments) of the present invention have been described above, but it goes without saying that the present invention is not limited to these embodiments, and various modifications and changes can be made within the scope of the present invention.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application is a continuation application of U.S. application Ser. No. 16/720,833 filed Dec. 19, 2019, the content of which is incorporated by reference herein. Additionally, this application claims the benefit of Japanese Patent Application No. 2018-245377 filed on Dec. 27, 2018, the content of which is also hereby incorporated by reference herein in its entirety.

What is claimed is:

1. A control apparatus configured to control radiation imaging by communicating with a radiation imaging apparatus having a plurality of imaging modes, comprising:
one or more controllers configured to (i) obtain first information with respect to a current imaging mode of the radiation imaging apparatus and second information with respect to a current communication state between the radiation imaging apparatus and the control apparatus, and (ii) cause a display device to display an indicator indicating a communication margin in the current communication state as information corresponding to any of multiple stages, based on the first information and the second information, wherein the multiple stages include at least a first stage with communication margin and a second stage with more communication margin than the first stage, the controllers are configured to cause the display device to display information corresponding to the first stage when the current imaging mode is the first imaging mode and the current communication state is a predetermined communication state, and the controllers are configured to cause the display device to display information corresponding to the second stage when the current imaging mode is the second imaging mode and the current communication state is the predetermined communication state.

2. The apparatus according to claim 1, wherein the controllers are configured to obtain a communication parameter in communication between the radiation imaging apparatus and the control apparatus as the information with respect to the communication state.

3. The apparatus according to claim 2, wherein the communication parameter includes at least one of a communication rate, a signal to noise ratio, a received signal strength indicator, and a communication delay time in the communication.

4. The apparatus according to claim 1, wherein the controllers are configured to obtain pieces of the information with respect to the communication state through a plurality of times of communication, and are configured to set a statistical value obtained from the obtained pieces of information with respect to the communication state as a representative value of the information with respect to the communication state.

5. The apparatus according to claim 4, wherein the controllers are configured to cause the display device to display, as the indicator indicating the margin in the communication state, a communication state level determined based on the set representative value of the information with respect to the communication state and the imaging mode of the radiation imaging apparatus.

6. A control apparatus configured to control radiation imaging by communicating with a radiation imaging apparatus having a plurality of imaging modes, comprising:

one or more controllers configured to cause a display device to display an indicator indicating a communication state level as information corresponding to any of multiple stages, based on first information with respect to current imaging mode of the radiation imaging apparatus and second information with respect to a current communication state between the radiation imaging apparatus and the control apparatus, wherein the multiple stages include at least a first stage and a second stage, the controllers are configured to cause the display state to display information corresponding to the first stage when the current imaging mode is in the first imaging mode and the current communication state is in a predetermined communication state, and the controllers are configured to cause the display device to display information corresponding to the second stage when the current imaging mode is the second imaging mode and the current communication state is the predetermined communication state.

7. The apparatus according to claim 6, wherein the controllers are configured to select one imaging mode from the plurality of imaging modes, and the controllers change the indicator indicating the communication state level based on the selected imaging mode, and cause the display device to display the changed indicator.

8. The apparatus according to claim 6, wherein the controllers configured to determine the communication state level based on the information with respect to the communication state and the selected imaging mode, the controllers are configured to hold a threshold table in which a threshold of the information with respect to the communication state for the communication state level is set for each of the plurality of imaging modes, and the controllers are configured to determine the communication state level from the threshold table based on the information with respect to the communication state and the imaging mode.

9. The apparatus according to claim 8, wherein the controllers are configured to cause the display device to display the indicator indicating the communication state level based on comparison between a threshold of the information with respect to the communication state required for communication set for each of the plurality of imaging modes and the obtained information with respect to the communication state.

10. The apparatus according to claim 8, wherein the controllers are configured to cause the display device to display a numerical value corresponding to the determined communication state level as the indicator indicating the communication state level.

11. The apparatus according to claim 8, wherein the controllers are configured to cause the display device to display a graphic pattern corresponding to the determined communication state level.

12. The apparatus according to claim 11, wherein the controllers are configured to change the graphic pattern in accordance with the communication state level, and cause the display device to display the changed graphic pattern.

13. The apparatus according to claim 11, wherein the controllers are configured to change a display color of the graphic pattern in accordance with the communication state level, and cause the display device to display the graphic pattern with the changed display color.

14. The apparatus according to claim 11, wherein the controllers are configured to perform display control of causing the display device to display the graphic pattern as the display of the indicator indicating the communication state level in a standard imaging mode, and the controllers are configured to change the display color of the graphic pattern as the display of the indicator indicating the margin in the selected imaging mode.

15. The apparatus according to claim 6, wherein communication between the radiation imaging apparatus and the control apparatus is wireless communication.

16. The apparatus according to claim 6, wherein communication between the radiation imaging apparatus and the control apparatus is wired communication.

17. The apparatus according to claim 6, wherein the radiation imaging apparatus includes a plurality of imaging pixels configured to obtain the radiation image, and a detection pixel configured to monitor irradiation of radiation, and the plurality of imaging modes include an AEC mode in which a start and a stop of irradiation of the radiation are controlled based on a dose of the radiation monitored by the detection pixel.

18. A radiation imaging apparatus having a plurality of imaging modes, and being communicated to a control apparatus configured to control radiation imaging, comprising:
one or more controllers configured to (i) obtain first information with respect to a current imaging mode of the radiation imaging apparatus and second information with respect to a current communication state between the radiation imaging apparatus and the control apparatus, and (ii) cause a display device to display an indicator indicating a communication state level as information corresponding to any of multiple stages, based on the first information and the second information, wherein
the multiple stages include at least a first stage and a second stage,
the controllers are configured to cause the display device to display information corresponding to the first stage when the current imaging mode is in the first imaging mode and the current communication state is a predetermined communication state, and
the controllers are configured to cause the display device to display information corresponding to the second stage when the current imaging mode is in the second imaging mode and the current communication state is in the predetermined communication state.

19. A control method of a control apparatus configured to control radiation imaging with a radiation imaging apparatus having a plurality of imaging modes, comprising:
obtaining first information with respect to a current imaging mode of the radiation imaging apparatus and second information with respect to a current communication state between the radiation imaging apparatus and the control apparatus; and
causing a display device to display an indicator indicating a margin in the current communication state as information corresponding to any of multiple stages, based on the first and second information, wherein
the multiple stages include at least a first stage with communication margin and a second stage with more communication margin than the first stage,
the controllers are configured to cause the display device to display information corresponding to the first stage when the current imaging mode is the first imaging mode and the current communication state is a predetermined communication state, and
the controllers are configured to cause the display device to display information corresponding to the second stage when the current imaging mode is the second imaging mode and the current communication state is the predetermined communication state.

20. A control method of a control apparatus configured to control radiation imaging by communicating with a radiation imaging apparatus having a plurality of imaging modes, comprising:
causing a display device to display an indicator indicating a communication state level as information corresponding to any of multiple stages, based on first information with respect to a current imaging mode of the radiation imaging apparatus and second information with respect to a current communication state between the radiation imaging apparatus and the control apparatus, wherein
the multiple stages include at least a first stage and a second stage,
the controllers are configured to cause the display device to display information corresponding to the first stage when the current imaging mode is the first imaging mode and the current communication state is a predetermined communication state, and
the controllers are configured to cause the display device to display information corresponding to the second stage when the current imaging mode is the second imaging mode and the current communication state is the predetermined communication state.

* * * * *